(12) United States Patent
Stroppolo et al.

(10) Patent No.: US 9,480,661 B2
(45) Date of Patent: Nov. 1, 2016

(54) SOLID DOSAGE FORMULATIONS CONTAINING WEIGHT-LOSS DRUGS

(75) Inventors: Federico Stroppolo, Aldesago (CH); Shahbaz Ardalan, Massagno (CH)

(73) Assignee: Alpex Pharma S.A., Mezzovico (CH)

( * ) Notice: Subject to any disclaimer, the term of this patent is extended or adjusted under 35 U.S.C. 154(b) by 1223 days.

(21) Appl. No.: 12/034,928

(22) Filed: Feb. 21, 2008

(65) Prior Publication Data

US 2008/0206327 A1 Aug. 28, 2008

Related U.S. Application Data

(60) Provisional application No. 60/902,521, filed on Feb. 22, 2007.

(51) Int. Cl.
| | | |
|---|---|---|
| *A61K 31/135* | (2006.01) | |
| *A61Q 9/00* | (2006.01) | |
| *A61K 9/00* | (2006.01) | |
| *A61K 9/20* | (2006.01) | |

(52) U.S. Cl.
CPC ........... *A61K 31/135* (2013.01); *A61K 9/0056* (2013.01); *A61K 9/2018* (2013.01)

(58) Field of Classification Search
None
See application file for complete search history.

(56) References Cited

U.S. PATENT DOCUMENTS

| | | | | |
|---|---|---|---|---|
| 5,502,080 A * | 3/1996 | Hitzig | ................. | A61K 31/135 514/654 |
| 6,149,938 A | 11/2000 | Bonadeo et al. | | |
| 6,177,101 B1 * | 1/2001 | Martino et al. | ................ | 424/464 |
| 6,323,236 B2 * | 11/2001 | McElroy | ....................... | 514/439 |
| 7,067,149 B1 * | 6/2006 | Chauveau et al. | ............ | 424/465 |
| 2004/0002462 A1 * | 1/2004 | Najarian | ................ | A61K 31/35 514/23 |
| 2004/0115258 A1 * | 6/2004 | Stroppolo et al. | ............ | 424/465 |
| 2005/0136112 A1 * | 6/2005 | Gonzales | ............. | A61K 9/0056 424/473 |
| 2005/0202084 A1 * | 9/2005 | Adusumilli et al. | .......... | 424/464 |
| 2006/0121112 A1 * | 6/2006 | Jenkins et al. | ................ | 424/468 |
| 2007/0082952 A1 * | 4/2007 | Benjamin | ..................... | 514/563 |

FOREIGN PATENT DOCUMENTS

| | | | |
|---|---|---|---|
| WO | WO9104757 | * | 4/1991 |
| WO | WO0027357 | * | 5/2000 |
| WO | WO2004080450 | * | 9/2004 |
| WO | WO2004098571 | * | 11/2004 |

OTHER PUBLICATIONS

Kaplan, Pharmacological Therapies for Obesity, Gastroenterol Clin N Am, 34 (2005) 91-104.*
Kokkinos et al, Possible association of ischemic stroke with phentermine, Stroke—Journal of the American Heart Association, 1993;24:310-313, http://stroke.ahajournals.org/content/24/2/310.*
First Amended Complaint, Alpex Pharma, S.A., *Citius Pharmaceuticals, LLC and Prenzamax, LLC v. Zydus Pharmaceuticals USA, Inc. and Cadila Healthcare Limited* (d/b/a Zydus Cadila) dated Aug. 1, 2013, 10 pages.
Guidance for Industry Orally Disintegrating Tablets, U.S. Department of Health and Human Services Food and Drug Administration, Center for Drug Evaluation and Research (CDER), Dec. 2008, 6 pages.
WebMD: Suprenza Oral Reviews and User Ratings: Effectiveness, Ease of Use, and Satisfaction, Jul. 7, 2014, 7 pages.

* cited by examiner

*Primary Examiner* — Jennifer Berrios
(74) *Attorney, Agent, or Firm* — Rothwell, Figg, Ernst & Manbeck, P.C.

(57) ABSTRACT

An orally disintegrating tablet which can be chewed or disintegrated by contact with saliva and containing weight-loss drugs for weight control in humans, especially in children and adolescents, is disclosed.

38 Claims, No Drawings

SOLID DOSAGE FORMULATIONS CONTAINING WEIGHT-LOSS DRUGS

FIELD OF THE INVENTION

The present invention relates to solid dosage formulations containing weight-loss drugs for weight control in humans, especially in children and adolescents. The formulations of the invention are orally disintegrating tablets which can be chewed or disintegrated by contact with saliva.

BACKGROUND OF THE INVENTION

The prevalence of overweight people in US has reached alarming levels. Also the proportion of children and adolescents who are overweight has tripled in the past three decades.

Obesity arises as a consequence of positive caloric balance. A comprehensive behavioral approach comprising a gradual increase of energy expenditure from exercise and an appropriate diet to decrease the caloric intake should be the more effective treatment of obesity.

However, this approach has a relatively low success rate. Consequently alternative forms of treatment, including surgery and/or medication, have been developed in an effort to increase the likelihood of achieving, and maintaining weight loss. In particular pharmacotherapy, in combination with intensive behavioral treatment, can lead to clinically significant decreases in body weight in obese population.

The FDA-approved weight-loss drugs are phentermine, sibutramine, orlistat and diethylpropion. Among them, phentermine is one of most efficient and safe in promoting weight loss especially when given along with recommendations for diet.

Phentermine is a sympathomimetic amine which first received approval from the FDA in 1959 as an appetite suppressant for the short-term treatment of exogenous obesity for patients with an initial body mass index ≥30 kg/m2, or ≥27 kg/m2 in the presence of other risk factors (e.g., hypertension, diabetes, hyperlipidemia).

Phentermine hydrochloride (α, α-dimethylphenethylamine hydrochloride) became available in the United States in the early seventies and is currently sold in several dosage form such as tablets, film coated tablets and capsules. Orally disintegrating tablets (ODT) which dissolve in the mouth for oral or sublingual administration are dosage forms particularly useful for patients with swallowing problems, for example children.

In particular, buccal tablets are intended for disintegrating in the mouth; the patient places them in the buccal cavity on the tongue or between cheeks and gums, thereby allowing a slow dissolution, which usually require 30-60 minutes (E. Rotteglia: "Compresse farmaceutiche" Societá Editoriale Farmaceutica, Milan, Italy, 1966).

On the contrary, sublingual tablets are intended to be placed under the tongue, where the active ingredient can be directly absorbed through the mucosa. These forms are provided with slow-disintegrating formulation as well (E. Rotteglia, ibid. and S. Casadio, Technologia Farmaceutica II Ed., Cisalpina Goliardica, Milan, Italy).

Orally disintegrating tablets with this kind of prolonged release are hardly suitable for formulating active ingredients, such as analgesics or anti inflammatory agents, which have to exert an immediate effect. Also, they are not always suitable for patients such as children or elderly people, and for the administration of active ingredients with an unpleasant taste because of the long stay in the mouth.

Sublingual tablets with a rapid dissolution profile can be prepared according to the Zydis® freeze-drying procedure. Zydis® is a registered trademark of R. P. Scherer Company (Manufacturing Chemist, February 1990). However, such formulations are very expensive and require sophisticated technologies and methods from the production point of view. These products are substantially freeze-dried products, the pharmaceutical formulation being therefore difficult to handle (due to its friability and fragility) and requiring specific packaging. A problem with freeze-dried sublingual tablet formulations is the impossibility to effect any taste-masking on the active ingredient.

WO088/08298 (Fuisz Technologies) discloses rapid-dissolution pharmaceutical composition in which the active ingredient is included in a water-soluble carrier obtained through a specific preparation process which requires a specific, expensive plant. Moreover, the resulting compositions exhibit friability problems and must always be handled and packed with particular precautions (use of dehydrating agents, humidity-tight packages, controlled-humidity work environmental and so on).

EP-A-494972 (Cima Labs Inc.) describes effervescent tablets suitable to the direct oral administration, i.e. without a previous development of the effervescence in water, consisting of microcapsules containing the active ingredients and an amount of effervescent agent sufficient to promote the release of microgranules when ingested and to give a "fizzing" sensation when in contact with the buccal mucosa of the patient.

In this case also, notwithstanding the presence of amounts of effervescent agent lower than in conventional formulations (60% by weight compared with the total composition) the typical cautions used for effervescent tablets should be taken.

Further drawbacks are the friability of the tablets and the use of microcapsules. In fact, the preparation technique described in EP-A-494972 does not foresee any wet granulation, i.e. using a solvent, but the direct mixing of the powder and its subsequent compression. Such a preparation technique yields tablets having friability values higher than those involving wet granulation of the mixture to be compressed.

SUMMARY OF THE INVENTION

In one aspect, the present invention relates to solid dosage formulations containing weight-loss drugs for weight control in humans, especially in children and adolescents.

In a further aspect, the present invention relates to orally disintegrating tablets, containing weight-loss drugs for weight control, which can be chewed or disintegrated by contact with saliva.

In a preferred embodiment, the present invention relates to orally disintegrating tablets containing phentermine or a pharmaceutically acceptable salt thereof in admixture with a pharmaceutically acceptable carrier. In a further preferred embodiment, the present invention relates to orally disintegrating tablets containing phentermine hydrochloride in admixture with a pharmaceutically acceptable carrier.

DETAILED DESCRIPTION OF EMBODIMENTS OF THE INVENTION

The present invention relates to solid dosage formulations, in particular orally disintegrating tablets, containing weight-loss drugs for weight control in humans, especially in children and adolescents.

Weight-loss drugs useful in the present invention include phentermine, sibutramine, orlistat, diethylpropion, and pharmaceutically acceptable salts thereof.

The weight-loss drugs useful in the present invention can be eventually used in combination with other active ingredients.

Orally disintegrating tablets containing phentermine or a pharmaceutically acceptable salt thereof are a preferred embodiment of the present invention, orally disintegrating tablets containing phentermine hydrochloride being still more preferred.

Preferably the solid dosage formulations of the present invention contain phentermine or a pharmaceutically acceptable salt thereof in an amount from about 2.5 mg to about 40 mg per dosage form.

More preferably, the solid dosage formulations of the present invention contain phentermine hydrochloride in an amount from about 2.5 mg to about 40 mg per dosage form, still more preferably in an amount from about 8 mg to about 37.5 mg per dosage form and more preferably from about 18 mg to about 36 mg per dosage form.

Orally disintegrating tablets containing phentermine hydrochloride in an amount of about 8 mg, about 15 mg, about 18 mg, about 22.5 mg, about 27 mg, about 30 mg, about 36 mg or about 37.5 mg are particularly preferred embodiments of the present invention.

The solid dosage formulations of the present invention contain the active ingredient in admixture with a pharmaceutically acceptable carrier.

The selection of the suitable pharmaceutically acceptable carrier should take into consideration several factors not only usually related to the formulation of an orally disintegrating tablet but also related to the therapeutic treatment which the formulation is to be used for and the patient population who will take the formulation.

In fact, orally disintegrating tablets containing weigh-loss drugs should have a pleasant taste for the whole period of disintegration in the mouth, a relatively short disintegration time, and avoid the presence of any component which could negatively affect the diet regimen often associated with the pharmacotherapy of obesity.

Pharmaceutically acceptable carriers useful for the orally disintegrating tablets according to the present invention preferably comprise one or more pharmaceutically acceptable excipients such as bulking agents, binders, disintegrating agents, acidifying agents, sweetening agents, lubricants, flavoring agents, and so on.

Specific examples of preferred bulking agents according to the present invention are polyalcohols, such as mannitol, sorbitol, lactose, lactitol, xylitol, erythritol, maltitol, and mixture thereof. Mannitol, lactose and mixture thereof are particularly preferred bulking agents according to the present invention.

The bulking agent is used in an amount from about 50% to about 95%, preferably from about 60% to about 90%, of the total weight of the orally disintegrating tablet according to the present invention.

Specific examples of preferred binders are polyvinylpyrrolidone (PVP), sodium carboxymethylcellulose, microcrystalline cellulose, and mixture thereof. In a preferred embodiment of the present invention, PVP is used as binder. The amount of binder is usually from about 0.5% to about 5%, preferably from about 0.8% to about 2%, of the total weight of the orally disintegrating tablet according to the present invention.

Specific preferred examples of disintegrating agents according to the present invention are maize starch, sodium starch glycolate, microcrystalline cellulose, sodium croscarmellose, calcium or sodium carboxymethylcellulose, crospovidone, and mixture thereof. Maize starch and crospovidone are the preferred disintegrating agents according to the present invention.

The preferred amount of disintegrating agent is from about 4% to about 10% by the total weight of the tablet according to the invention. More preferably the amount of disintegrating agent is from about 5% to about 8% by the total weight of the tablet according to the present invention.

Acidifying agents useful in the orally disintegrating tablets according to the present invention include citric acid, fumaric acid, malic acid, tartaric acid, and mixture thereof.

The preferred acidifying agent is citric acid, still more preferable being the use of citric acid in an amount from about 2% to about 8% of the total weight of the orally disintegrating tablet of the present invention.

Sweetening agents useful in the formulation of the present invention are artificial sweetener such as aspartame, saccharin, sucralose and mixture thereof. Aspartame and sucralose are the preferred sweetening agents in the formulation of the present invention.

The amount of sweetening agent is preferably from about 0.5% to about 5%, more preferably from about 0.8% to about 2%, of the total weight of the orally disintegrating tablet according to the present invention.

Specific examples of lubricants which can be used in the formulation according to the present invention are calcium stearate, magnesium stearate, magnesium trisilicate, sodium stearyl fumarate, stearic acid, zinc stearate, and mixture thereof.

Magnesium stearate is the preferably used lubricant according to the present invention. The amount of magnesium stearate is generally from about 0.1% to about 1.0%, preferably from about 0.5% to about 1.0% of the total weight of the tablet.

The flavoring agents are selected from synthetic or natural flavors, extracts from plants or flowers, essential oil such as cinnamon, peppermint, clove, anise, eucalyptus, thyme, cedar, chamomile oils, fruit essences such as apple, peach, strawberry, raspberry, orange, apricot, cherry, plum, pineapple, or mixture thereof.

The amount of flavoring agent can vary depending on the selected flavor and on the desired organoleptic effect. Usually, the amount of flavoring agent is from about 0.5% to about 3.0% of the total weight of the tablet.

In the orally disintegrating tablet according to the present invention, mint flavor is the preferably used flavoring agent for its anesthetic and taste-masking effect even in low amounts, i.e. about 0.5-1.0% of the total weight of the tablet.

The orally disintegrating tablets according to the present invention can optionally contain one or more pharmaceutically acceptable coloring agents, preferably from about 0.01% to about 0.5% of the total weight of the tablet.

A particularly preferred embodiment of the present invention is an orally disintegrating tablet with the following composition:

| | |
|---|---|
| Phentermine HCl | 2-5% w/w |
| Mannitol | 20-45% w/w |
| Aspartame | 0.5-5% w/w |
| Maize Starch | 4-10% w/w |
| Citric Acid | 2-5% w/w |
| Lactose | 25-65% w/w |
| PVP | 0.5-5% w/w |

-continued

| | |
|---|---|
| Magnesium Stearate | 0.1-1% w/w |
| Flavor | 0.5-3% w/w |
| the total being | 100% |

Another particularly preferred embodiment of the present invention is an orally disintegrating tablet with the following composition:

| | |
|---|---|
| Phentermine HCl | 2-5% w/w |
| Mannitol | 60-90% w/w |
| Sucralose | 0.5-5% w/w |
| Crospovidone | 4-10% w/w |
| Citric Acid | 2-8% w/w |
| PVP | 0.5-5% w/w |
| Magnesium Stearate | 0.1-1% w/w |
| Flavor | 0.5-3% w/w |
| Coloring agent | 0.01-0.5% w/w |
| the total being | 100% |

The orally disintegrating tablets according to the present invention can be prepared according to conventional formulation technologies, such as sieving, granulation, drying, blending and compression.

In a preferred practical embodiment, the manufacturing process of the solid dosage forms according to the present invention is the following.

The active ingredient, the bulking agent, the sweetening agent, the disintegrating agent and the acidifying agent are granulated with an aqueous solution containing the binder in a suitable fluid bed granulator. The flavoring agent and the lubricant are added to the external phase and the resultant mixture is blended in a suitable mixer. The blended mixture is then compressed in a tabletting machine with punches of the desired shape obtaining the orally disintegrating tablets according to the present invention in the selected strength.

Preferably the orally disintegrating tablets of the present invention have a toroidal or round shape with a diameter from about 10 mm to about 16 mm, a total weight from about 200 mg to about 1000 mg and a strength from about 2 mg to about 40 mg, preferably from about 8 mg to about 37.5 mg, still more preferably of about 15 mg, about 18 mg, about 27 mg, about 30 mg, about 36 mg, and about 37.5 mg.

The orally disintegrating tablets according to the present invention are stable, easy to be administered because they require just to be chewed or disintegrated by contact with saliva and the disintegration time is relatively quick (usually about 15 minutes or less).

The tablet of the invention can be taken without water but there is no swallowing problem because the drug is swelled in the form of solution or suspension and the unpleasant taste of the active ingredient is efficiently masked during the whole swallowing phase.

The advantageous properties of the orally disintegrating tablets of the present invention make them particularly in compliance with the need of the overweight patients, especially with children and adolescents.

The following examples better illustrate the present invention without limiting it.

Example 1

Preparation of an Orally Disintegrating Tablet Containing Phentermine Hydrochloride Phentermine hydrochloride (supplied by Siegfried, NJ-US; Alpex analysis no. RM008/04), mannitol (supplied by Roquette Fréres, Lestrem—France Alpex analysis no. RM004/04), aspartame (supplied by Ajinomoto—Gravelines—France; Alpex analysis no. 2204MP), citric acid (supplied by DSM, Basel—Switzerland; Alpex analysis no. RM005/04), lactose powder DCI 21 (DMV-Northenhardenberg—Germany; Alpex analysis no. RM009/04), and maize starch (supplied by Roquette Fréres, France; Alpex analysis no. RM002/04) were sieved and granulated with an aqueous solution of Kollidon K30 (supplied by BASF, Germany; Alpex analysis no. RM007/04) using an Aeromatic Strea-1 fluid bed granulator. Mint flavor (supplied by Firmenich Switzerland; Alpex analysis no. RM006/04) and magnesium stearate (supplied i.e by Faci-Genoa, Italy; Alpex analysis no. RM003/04) were added to the external phase and the mixture was blended for 10 minutes at 20 rpm with Erweka cube mixer. The blended mixture were then compressed by Ronchi CT20 single punch tabletting machine, in toroidal shaped tablets, 16 mm in diameter, having the following composition:

| | |
|---|---|
| Phentermine HCl | 37.5 mg |
| Mannitol | 250.0 mg |
| Aspartame | 10.0 mg |
| Maize Starch | 60.0 mg |
| Citric Acid | 40.0 mg |
| Lactose | 579.5 mg |
| PVP K30 | 10.0 mg |
| Magnesium Stearate | 8.0 mg |
| Mint flavor | 5.0 mg |
| TOTAL WEIGHT | 1000.0 mg |

Example 2

Following the procedure described in Example 1, orally disintegrating tablets, in toroidal shape, 14 mm in diameter, having the following composition were prepared:

| | |
|---|---|
| Phentermine HCl | 36.00 mg |
| Mannitol | 240.00 mg |
| Aspartame | 9.60 mg |
| Maize Starch | 57.60 mg |
| Citric Acid | 38.40 mg |
| Lactose | 556.32 mg |
| PVP K30 | 9.60 mg |
| Magnesium Stearate | 7.68 mg |
| Mint flavor | 4.80 mg |
| TOTAL WEIGHT | 960.00 mg |

Example 3

Following the procedure described in Example 1, orally disintegrating tablets, in toroidal shape, 15 mm in diameter, having the following composition were prepared:

| | |
|---|---|
| Phentermine HCl | 27.00 mg |
| Mannitol | 180.00 mg |
| Aspartame | 7.20 mg |
| Maize Starch | 43.20 mg |
| Citric Acid | 28.80 mg |
| Lactose | 417.24 mg |
| PVP K30 | 7.20 mg |
| Magnesium Stearate | 5.76 mg |
| Mint flavor | 3.60 mg |
| TOTAL WEIGHT | 720.00 mg |

Example 4

Following the procedure described in Example 1, orally disintegrating tablets, in toroidal shape, 14 mm in diameter, having the following composition were prepared:

| | |
|---|---|
| Phentermine HCl | 22.5 mg |
| Mannitol | 150.0 mg |
| Aspartame | 6.0 mg |
| Maize Starch | 36.0 mg |
| Citric Acid | 24.0 mg |
| Lactose | 347.7 mg |
| PVP K30 | 6.0 mg |
| Magnesium Stearate | 4.8 mg |
| Mint flavor | 3.0 mg |
| TOTAL WEIGHT | 600.0 mg |

Example 5

Following the procedure described in Example 1, orally disintegrating tablets, in toroidal shape, 13 mm in diameter, with the following composition were prepared:

| | |
|---|---|
| Phentermine HCl | 18.00 mg |
| Mannitol | 120.00 mg |
| Aspartame | 4.80 mg |
| Maize Starch | 28.80 mg |
| Citric Acid | 19.20 mg |
| Lactose | 278.16 mg |
| PVP K30 | 4.80 mg |
| Magnesium Stearate | 3.84 mg |
| Mint flavor | 2.40 mg |
| TOTAL WEIGHT | 480.00 mg |

Example 6

Following the procedure described in Example 1, orally disintegrating tablets, in toroidal shape, 10 mm in diameter, with the following composition were prepared:

| | |
|---|---|
| Phentermine HCl | 8.00 mg |
| Mannitol | 53.33 mg |
| Aspartame | 2.13 mg |
| Maize Starch | 12.80 mg |
| Citric Acid | 8.53 mg |
| Lactose | 123.63 mg |
| PVP K30 | 2.13 mg |
| Magnesium Stearate | 1.71 mg |
| Mint flavor | 1.07 mg |
| TOTAL WEIGHT | 213.33 mg |

Example 7

Following the procedure described in Example 1, orally disintegrating tablets, in round embossed shape, 14 mm in diameter, with the following composition were prepared:

| | |
|---|---|
| Phentermine HCl | 37.500 mg |
| Mannitol powder | 410.000 mg |
| Sucralose | 5.500 mg |
| Citric Acid powder | 40.000 mg |
| Povidone CL | 30.000 mg |
| PVP K30 | 6.000 mg |
| Magnesium Stearate | 6.000 mg |
| Mannitol pregranulated | 59.880 mg |
| Peppermint flavor | 5.000 mg |
| Blue FD&C#1 | 0.120 mg |
| TOTAL WEIGHT | 600.000 mg |

Example 8

Following the procedure described in Example 1, orally disintegrating tablets, in round embossed shape, 14 mm in diameter, with the following composition were prepared:

| | |
|---|---|
| Phentermine HCl | 30.000 mg |
| Mannitol powder | 356.300 mg |
| Sucralose | 5.500 mg |
| Citric Acid powder | 40.000 mg |
| Povidone CL | 30.000 mg |
| PVP K30 | 6.000 mg |
| Magnesium Stearate | 6.000 mg |
| Mannitol pregranulated | 120.000 mg |
| Peppermint flavor | 5.000 mg |
| Yellow FD&C#5 | 1.200 mg |
| TOTAL WEIGHT | 600.000 mg |

Example 9

Following the procedure described in Example 1, orally disintegrating tablets, in round embossed shape, 10 mm in diameter, with the following composition were prepared:

| | |
|---|---|
| Phentermine HCl | 15.000 mg |
| Mannitol powder | 178.150 mg |
| Sucralose | 2.750 mg |
| Citric Acid powder | 20.000 mg |
| Povidone CL | 15.000 mg |
| PVP K30 | 3.000 mg |
| Magnesium Stearate | 3.000 mg |
| Mannitol pregranulated | 59.880 mg |
| Peppermint flavor | 2.500 mg |
| Yellow FD&C#5 | 0.600 mg |
| Blue FD&C#1 | 0.120 mg |
| TOTAL WEIGHT | 300.000 mg |

Example 10

Determination of the Physico-Chemical Characteristics of Orally Disintegrating Tablets Containing Phentermine Hydrochloride Orally disintegrating tablets containing phentermine hydrochloride in different strengths, prepared according to the procedure described in example 1 were analyzed and the analytical results are reported in Table 1.

TABLE 1

Physico-chemical values of orally disintegrating tablets containing phentermine HCl at different strengths

| | Dosage strength (mg/tablet) | | | | | |
|---|---|---|---|---|---|---|
| | 37.5 | 36.0 | 27.0 | 22.5 | 18.0 | 8.0 |
| Tablet diameter | 16 | 16 | 15 | 14 | 13 | 10 |
| Appearance | white toroidal tablets | | | | | |
| Disintegration time in vitro | NMT 15 minutes | | | | | |
| Average weight (AW) (mg) | 950-1050 | 912-1008 | 684-756 | 570-630 | 456-504 | 203-224 |
| Uniformity of weight | not more than 2/20 tablets = AW ± 5 none of 20/20 tablets = AW ± 5% | | | | | |
| Hardness (Kp) | 2-10 | | | | | |
| Thickness (mm) | 4.4-5.6 | 4.3-5.5 | 4.0-5.6 | 3.2-4.4 | 3.2-5.6 | 2.3-3.5 |
| Moisture (KF) | not more than 1.0% w/w | | | | | |
| Dissolution test | NTL 90% after 10 minutes | | | | | |
| Identification of phentermine HCl | positive | | | | | |
| Assay of phentermine HCl (mg/tablet) | 33.75-41.25 | 32.4-39.6 | 24.3-29.7 | 20.25-24.75 | 16.2-19.8 | 7.2-8.8 |
| Content uniformity of tablet | (90.0-110.0% of the claim) complies | | | | | |
| Related impurities and degradants | A 2-methyl-1-phenyl-2-propanol | | | | NMT 0.5% | |
| | B benzyl alcohol | | | | NMT 0.5% | |
| | C 3,4-dihydro-3,3-dimethylsequinolone | | | | NMT 0.5% | |
| | D 2-methyl-1-phenyl-1-propene | | | | NMT 0.5% | |
| | any individual unknown impurity | | | | NMT 0.2% | |
| | total impurities | | | | NMT 1.0% | |
| Microbial limits | total aerobic microbial count | | | | <$10^3$ UFC/g | |
| | E. coli | | | | <$10^2$ UFC/g | |
| | Molds and yeasts count | | | | absent/10 g | |

What is claimed is:

1. An orally disintegrating tablet consisting of one weight-loss drug for weight control in admixture with a pharmaceutically acceptable carrier, wherein the weight loss drug is phentermine HCl, and wherein said orally disintegrating tablet disintegrates in about 15 minutes or less when contacted with saliva.

2. An orally disintegrating tablet according to claim 1 wherein the drug is present in an amount of from about 2.5 mg to about 40 mg per dosage form.

3. An orally disintegrating tablet according to claim 1 wherein said phentermine hydrochloride is in an amount of from about 8 mg to about 37.5 mg per dosage form.

4. An orally disintegrating tablet according to claim 3 wherein the phentermine hydrochloride is present in an amount of about 8 mg, about 15 mg, about 18.0 mg, about 22.5 mg, about 27 mg, about 30 mg, about 36.0 mg or about 37.5 mg.

5. An orally disintegrating tablet according to claim 1 wherein the pharmaceutically acceptable carrier is selected from the group consisting of one or more of the following pharmaceutically acceptable excipients: a bulking agent, a binder, a disintegrating agent, an acidifying agent, a sweetening agent, a lubricant, and a flavoring agent.

6. An orally disintegrating tablet according to claim 5 wherein the bulking agent comprises a polyalcohol selected from the group consisting of one or more of mannitol, sorbitol, lactose, lactitol, xylitol, erythritol, maltitol, and mixtures thereof.

7. An orally disintegrating tablet according to claim 5 wherein the bulking agent is present in an amount of from about 50% to about 95% of the total weight of the tablet.

8. An orally disintegrating tablet according to claim 7 wherein the bulking agent is present in an amount of from about 60% to about 90% of the total weight of the tablet.

9. An orally disintegrating tablet according to claim 5 wherein the bulking agent comprises mannitol, lactose or mixture thereof.

10. An orally disintegrating tablet according to claim 5 wherein the binder comprises polyvinylpyrrolidone, sodium carboxymethylcellulose, microcrystalline cellulose, or mixtures thereof.

11. An orally disintegrating tablet according to claim 10 wherein the amount of binder is from about 0.5% to about 5% of the total weight of the tablet.

12. An orally disintegrating tablet according to claim 11 wherein the amount of binder is from about 0.8% to about 2% of the total weight of the tablet.

13. An orally disintegrating tablet according to claim 10 wherein the binder comprises polyvinylpyrrolidone.

14. An orally disintegrating tablet according to claim 5 wherein the disintegrating agent comprises maize starch, sodium starch glycolate, microcrystalline cellulose, sodium croscarmellose, calcium or sodium carboxymethylcellulose, crospovidone, or mixtures thereof.

15. An orally disintegrating tablet according to claim 14 wherein the amount of disintegrating agent is from about 4% to about 10% of the total weight of the tablet.

16. An orally disintegrating tablet according to claim 15 wherein the amount of disintegrating agent is from about 5% to about 8% by the total weight of the tablet.

17. An orally disintegrating tablet according to claim 14 wherein the disintegrating agent comprises maize starch or crospovidone.

18. An orally disintegrating tablet according to claim 5 wherein the acidifying agent comprises citric acid, fumaric acid, malic acid, tartaric acid, or mixtures thereof.

19. An orally disintegrating tablet according to claim 18 wherein the acidifying agent comprises citric acid.

20. An orally disintegrating tablet according to claim 19 wherein the amount of acidifying agent is from about 2% to about 8% of the total weight of the tablet.

21. An orally disintegrating tablet according to claim 5 wherein the sweetening agent is an artificial sweetener which comprises aspartame, saccharin, sucralose, or mixtures thereof.

22. An orally disintegrating tablet according to claim 21 wherein the amount of sweetening agent is from about 0.5% to about 5% of the total weight of the tablet.

23. An orally disintegrating tablet according to claim 22 wherein the amount of sweetening agent is from about 0.8% to about 2% of the total weight of the tablet.

24. An orally disintegrating tablet according to claim 21 wherein the sweetening agent comprises aspartame or sucralose.

25. An orally disintegrating tablet according to claim 5 wherein the lubricant comprises calcium stearate, magnesium stearate, magnesium trisilicate, sodium stearyl fumarate, stearic acid, zinc stearate, or mixtures thereof.

26. An orally disintegrating tablet according to claim 25 wherein the lubricant comprises magnesium stearate.

27. An orally disintegrating tablet according to claim 26 wherein the amount of magnesium stearate is from about 0.1% to about 1.0% of the total weight of the tablet.

28. An orally disintegrating tablet according to claim 26 wherein the amount of magnesium stearate is from about 0.5% to about 1.0% of the total weight of the tablet.

29. An orally disintegrating tablet according to claim 5 wherein the flavoring agent comprises synthetic or natural flavors, extracts from plants or flowers, essential oil such as cinnamon, peppermint, clove, anise, eucalyptus, thyme, cedar, chamomile oils, fruit essences such as apple, peach, strawberry, raspberry, orange, apricot, cherry, plum, pineapple, or mixtures thereof.

30. An orally disintegrating tablet according to claim 29 wherein the amount of flavoring agent is from about 0.5% to about 3.0% of the total weight of the tablet.

31. An orally disintegrating tablet according to claim 29 wherein the flavoring agent comprises mint flavor.

32. An orally disintegrating tablet according to claim 29 wherein the amount of flavoring agent is from about 0.5% to about 1.0% of the total weight of the tablet.

33. An orally disintegrating tablet according to claim 5 consisting of:

| | |
|---|---|
| phentermine HCl | 2-5% w/w |
| mannitol | 20-45% w/w |
| aspartame | 0.5-5% w/w |
| maize starch | 4-10% w/w |
| citric acid | 2-5% w/w |
| lactose | 25-65% w/w |
| PVP | 0.5-5% w/w |
| magnesium stearate | 0.1-1% w/w |
| flavor | 0.5-3% w/w |
| the total being | 100%. |

34. An orally disintegrating tablet according to claim 5 consisting of:

| | |
|---|---|
| Phentermine HCl | 2-5% w/w |
| Mannitol | 60-90% w/w |
| Sucralose | 0.5-5% w/w |
| Crospovidone | 4-10% w/w |
| Citric Acid | 2-8% w/w |
| PVP | 0.5-5% w/w |
| Magnesium Stearate | 0.1-1% w/w |
| Flavor | 0.5-3% w/w |
| Coloring agent | 0.01-0.5% w/w |
| the total being | 100%. |

35. Method of treatment of obesity in a child or adolescent patient in need of such treatment, the method comprising orally administering to the patient an anti-obesity effective amount of an orally disintegrating tablet according to claim 1.

36. An orally disintegrating tablet consisting of about 8 mg, about 15 mg, about 18.0 mg, about 22.5 mg, about 27 mg, about 30 mg, about 36.0 mg or about 37.5 mg phentermine HCl as a pharmaceutically active ingredient, and further consisting of as orally disintegrating formulation agents: Mannitol powder; Mannitol pregranulated; Sucralose; Citric Acid; Peppermint flavor; PVP K30; Povidone CL; Magnesium Stearate; Coloring agent; Talc; and Sodium Lauryl sulfate, said pharmaceutically active ingredient and said orally disintegrating formulation agents being 100% w/w of said orally disintegrating tablet, and wherein said orally disintegrating tablet disintegrates in about 15 minutes or less when contacted with saliva.

37. An orally disintegrating tablet consisting of Phentermine HCl, 60-90% w/w mannitol, 0.5-5% w/w sucralose, 2-8% w/w citric acid, 0.5-3% w/w flavor, 0.01-0.5% w/w coloring agent, 4-10% w/w crospovidone, 0.5-5% w/w PVP and one or more of magnesium stearate, talc and sodium lauryl sulfate, the total being 100%, and wherein said orally disintegrating tablet disintegrates in about 15 minutes or less when contacted with saliva.

38. A tablet consisting of one drug for weight control in admixture with a pharmaceutically acceptable carrier suitable for use in an orally disintegrating tablet (ODT), wherein said drug for weight control consists of phentermine HCl, and wherein said tablet is in a dosage form which disintegrates in about 15 minutes or less without chewing when contacted with saliva.

* * * * *